United States Patent
Yoshioka

(10) Patent No.: US 9,526,823 B2
(45) Date of Patent: Dec. 27, 2016

(54) CELL TREATMENT DEVICE, CELL TREATMENT CARTRIDGE AND BODY FLUID TREATMENT SYSTEM

(75) Inventor: Satomi Yoshioka, Shiojiri (JP)

(73) Assignee: Seiko Epson Corporation (JP)

( * ) Notice: Subject to any disclaimer, the term of this patent is extended or adjusted under 35 U.S.C. 154(b) by 1181 days.

(21) Appl. No.: 12/720,927

(22) Filed: Mar. 10, 2010

(65) Prior Publication Data

US 2010/0248338 A1    Sep. 30, 2010

(30) Foreign Application Priority Data

Mar. 27, 2009 (JP) ................................. 2009-078455

(51) Int. Cl.
  *C12M 1/00* (2006.01)
  *A61M 1/36* (2006.01)
  *C12M 1/42* (2006.01)

(52) U.S. Cl.
  CPC ......... *A61M 1/3679* (2013.01); *A61M 1/3687* (2013.01); *A61M 1/3689* (2014.02); *B01L 2200/0668* (2013.01); *C12M 35/02* (2013.01)

(58) Field of Classification Search
  CPC .................. B01L 2200/0668; C12Q 2527/137; C12M 35/02
  See application file for complete search history.

(56) References Cited

U.S. PATENT DOCUMENTS

| | | | |
|---|---|---|---|
| 4,894,343 A * | 1/1990 | Tanaka et al. | ............ 435/285.2 |
| 2002/0045272 A1* | 4/2002 | McDevitt et al. | ............ 436/518 |
| 2002/0172987 A1 | 11/2002 | Terstappen et al. | |
| 2007/0037172 A1 | 2/2007 | Chiu et al. | |
| 2008/0248499 A1 | 10/2008 | Chiu et al. | |
| 2010/0279321 A1 | 11/2010 | Chiu et al. | |

FOREIGN PATENT DOCUMENTS

| | | |
|---|---|---|
| JP | 2000-023657 | 1/2000 |
| JP | 2005-010177 | 1/2005 |
| JP | 2007-222132 | 9/2007 |
| JP | 2009-504154 | 2/2009 |

OTHER PUBLICATIONS

Cross, Sarah E. et al., AFM-based analysis of human metastatic cancer cells, Department of Chemistry and Biochemistry, University of California, Los Angeles, Aug. 12, 2008, pp. 1-8.

* cited by examiner

*Primary Examiner* — Jonathan Hurst
(74) *Attorney, Agent, or Firm* — Harness, Dickey & Pierce, P.L.C.

(57) ABSTRACT

A cell treatment device which allows cell dispersion liquid including cancer cells to pass therethrough to cause at least the cancer cells to be subjected to at least one of a physical action, a chemical action, and a biologically activating action, includes: a slit member having a first surface and a second surface and including a through hole having a slit shape penetrating from the first surface to the second surface and extending in one direction, the through hole having a tapered portion, wherein the width of a cross section of the tapered portion orthogonal in the one direction reduces from the first surface toward the second surface side, and is smaller than an average diameter of the cancer cells at an end on the second surfaces side, and the cell dispersion liquid is allowed to pass from the first surface side through the through hole to the second surface side.

17 Claims, 7 Drawing Sheets

CELL TREATMENT DEVICE, CELL TREATMENT CARTRIDGE AND BODY FLUID TREATMENT SYSTEM

Japanese Patent Application No. 2009-078455 filed on Mar. 27, 2009, is hereby incorporated by reference in its entirety.

BACKGROUND

1. Technical Field

The present invention relates to a cell treatment device, a cell treatment cartridge and a body fluid treatment system.

2. Related Art

In the related art, a method of administering an anti-cancer agent or a method of irradiating with a radioactive ray has been employed as a method of attacking cancer. Also, in recent years, as a further advanced method, a method of using an antibody/molecules target medicine, a method of using a cancer vaccine, and a method of using a gene manipulation are under development. Although these methods are intended to attack the cancer, a sufficient effect cannot necessarily be obtained regarding the metastasis of cancer.

Death of human being due to cancer is caused by the metastasis of the cancer in many cases. In general, the metastasis of cancer is considered to occur in the following manner. First of all, cancer cells which form cancer of a primary focus invade a blood vessel or a lymph duct. Subsequently, the cancer cells having invaded the blood vessel and the lymph dust are transferred by a flow of blood or lymph fluid. Subsequently, the transferred cancer cells are fixed on and infiltrated into a tube wall of a separate tissue or the like apart from the primary focus. Then, new cancer (metastatic focus) is formed in the separate tissue or the like.

The cancer cells circulating in a human body through the blood vessel are referred to as a circulating cancer cell (CTC: Circulating Tumor Cell). For example, in JP-A-2005-010177, a method of isolating the circulating cancer cells and a reagent are disclosed. In the same publication, there is description saying that the circulating cancer cells can be separated and counted efficiently by causing magnetic particles including ligand molecules which bind specifically to the cancer cells to trap the cancer cells.

JP-A-2005-010177 is an example of related art.

However, in the method of attacking cancer, attacking normal cells simultaneously cannot be avoided, and the normal cells are damaged. Therefore, maintaining QOL (Quality Of Life) of patients high is difficult.

The method of isolating circulating cancer cells is intended to diagnose for early detection of cancer. In this method, blood is used as a sample, and foreign substances such as magnetic particles or the like are added. Therefore, the blood used for the diagnosis is difficult to use as blood preparation. When such a method is applied for removing the circulating cancer cells from the blood, it means that the foreign substances are mixed to the blood and, when such the blood is administered, there is the danger such as remarkable lowering of the QOL or the risk of the patient's life.

SUMMARY

An advantage of some aspects of the invention is to provide a cell treatment device which is capable of providing at least one of a physical action, a chemical action, and a biologically activating action efficiently to at least cancer cells included in cell dispersion liquid such as blood or the like.

Another advantage of some aspects of the invention is to provide a cell treatment device which is capable of subjecting immune cells included in cell dispersion liquid to the biologically activating action efficiently.

The invention can solve at least part of the problems described above, and may be realized in the following modes or application example.

First Aspect

A first aspect of the invention is directed to a cell treatment device which allows cell dispersion liquid including cancer cells to pass therethrough to cause at least the cancer cells to be subjected to at least one of a physical action, a chemical action, and a biologically activating action, including: a slit member having a first surface and a second surface and including a through hole having a slit shape penetrating from the first surface to the second surface and extending in one direction, the through hole having a tapered portion, in which the width of a cross section of the tapered portion orthogonal in the one direction reduces from the first surface toward the second surface side, and is smaller than an average diameter of the cancer cells at an end on the second surfaces side, and the cell dispersion liquid is allowed to pass from the first surface side through the through hole to the second surface side.

The cell treatment device as such is capable of bringing the cancer cells into at least contact with the surface of the slit member. Accordingly, at least the physical action such as trapping and collecting the cancer cell may be achieved. Also, since the through hole has a slit-type shape, the through hole is hardly be clogged even after having trapped the cancer cell, and hence a flow channel for the cell dispersion liquid is sufficiently secured.

Second Aspect

A second aspect of the invention is directed to the cell treatment device according to the first aspect, wherein the first surface and the second surface are parallel to each other.

The cell treatment device according to the second aspect has the flat panel-shaped slit member, and hence is advantageous in that downsizing is possible and manufacture is easy are achieved, in addition to the advantage of the cell treatment device according to the first aspect.

Third Aspect

A third aspect of the invention is directed to the cell treatment device according to the first aspect, wherein the first surface and the second surface are cylindrical surfaces having a single axis as a center axis.

The cell treatment device according to the third aspect has the cylindrical slit member, and hence is advantageous in that downsizing is possible and manufacture is easy are achieved, in addition to the advantage of the cell treatment device according to the first aspect.

Fourth Aspect

A fourth aspect of the invention is directed to the cell treatment device according to any of the first to third aspects, wherein the through hole further includes a narrowed portion, the narrowed portion continues to an end of the tapered portion on the second surface side, and the width of a cross section of the narrowed portion orthogonal in the one direction is the cross section of the width of the tapered portion at the end on the second surface side or smaller.

The cell treatment device according to the fourth aspect includes the narrowed portion of a certain length in a flowing rout of the cell dispersion liquid, whereby a flow channel having a smaller diameter than an average diameter of the cancer cells is elongated. Therefore, the action to trap and collect the cancer cells is further enhanced, and the cancer cells can be brought into contact with the surface of the slit member easily.

Fifth Aspect

A fifth aspect of the invention is directed to the cell treatment device according to the fourth aspect, the narrowed portion includes a first area on the first surface side and a second area on the second surface side, and the width of a cross section of the second area orthogonal in the one direction is smaller than an average diameter of the immune cells included in the cell dispersion liquid.

The cell treatment device according to the fifth aspect includes the second area having a width smaller than the average diameter of the immune cells in the narrowed portion. Therefore, the cell treatment device according to the fifth aspect is advantageous in that the immune cells can be brought into contact with the surface of the slit member easily, in addition to the advantage of the cell treatment device according to the fourth aspect.

Sixth Aspect

A sixth aspect of the invention is directed to the cell treatment device according to the fifth aspect, wherein an immune cell activating factor which acts specifically on the immune cells is fixed to the surface of the slit member which forms the second area.

The cell treatment device according to the sixth aspect is capable of bringing the immune cells into contact with the immune cell activating factor at a high frequency.

Seventh Aspect

A seventh aspect of the invention is directed to the cell treatment device according to any of the fourth to sixth aspects, wherein a cytokine which acts on the cancer cells are fixed to the surface of the slit member which forms the narrowed portion.

The cell treatment device as such is capable of bringing the cancer cells into contact with the cytokine at a high frequency. Accordingly, the cancer cells are efficiently subjected to the chemical action or the biologically activating action. Since the frequency of contact between the cytokine and the cancer cells in the narrowed portion is high, the quantity of the cytokine with respect to the cell dispersion liquid may be small.

Eighth Aspect

An eighth aspect of the invention is directed to the cell treatment device according to the seventh aspect, wherein the cytokine is an apoptosis factor.

The cell treatment device according to the eighth aspect is capable of bringing the cancer cells into contact with the apoptosis factor at a high frequency. Accordingly, the effect to cause the cancer cells to fall into apoptosis (cause the cancer cells to be subjected to the biologically activating action) may be achieved quite efficiently. Since the frequency of contact between the apoptosis factor and the cancer cells is high, the quantity of the apoptosis factor with respect to the cell dispersion liquid may be small.

Ninth Aspect

A ninth aspect of the invention is directed to the cell treatment device according to any of the first to eighth aspects, wherein the through hole further has an inverted tapered portion, the inverted tapered portion continues to an end of the tapered portion or the narrowed portion on the second surface side, and the width of a cross section of the inverted tapered portion orthogonal in the one direction increases from the first surface side toward the second surface.

The cell treatment device according to the ninth aspect is capable of restraining the cell dispersion liquid from staying on the second surface side. Accordingly, for example, coagulation may be restrained when the cell dispersion liquid is blood.

Tenth Aspect

A tenth aspect of the invention is directed to the cell treatment device according to any of first to ninth aspects, wherein an antibody which acts specifically on the cancer cells is fixed to the surface of the slit member which forms the tapered portion.

The cell treatment device according to the tenth aspect is capable of causing the cancer cells to stay in the tapered portion. Accordingly, the physical action such as lowering the velocity of movement of the cancer cells may be achieved. When the antibody only is fixed on the surface of the slit member which forms the tapered portion, the quantity of the antibody with respect to the cell dispersion liquid may be small.

Eleventh Aspect

An eleventh aspect of the invention is directed to the cell treatment device according to any of the first to tenth aspects, wherein the surface of the slit member which forms the tapered portion includes a groove.

The cell treatment device according to the eleventh aspect is capable of causing turbulence in the flow of the cell dispersion liquid in the tapered portion. Accordingly, contact of the cancer cells or the immune cells with the surface of the slit member which constitutes the tapered portion may be facilitated.

Twelfth Aspect

A twelfth aspect of the invention is directed to the cell treatment device according to any of the first to eleventh aspects, wherein a coating having at least one of functions selected from hydrophilic nature, water repellency, and blocking tendency is applied on the surface of the slit member.

The cell treatment device according to the twelfth aspect is capable of preventing the cells from sticking nonspecifically fast to the surface of the slit member when the cell dispersion liquid passes therethrough. Accordingly, the resistance generated when the cell dispersion liquid passes therethrough may be restrained. For example, in a case where the cell dispersion liquid is blood, cells other than the cancer cells and immune cells are restrained from sticking fast to the surface of the slit member, so that clogging of the cell treatment device is restrained.

Thirteenth Aspect

A thirteenth aspect of the invention is directed to the cell treatment device according to any of the first to twelfth aspects, wherein the slit member is formed with a plurality of the through holes extending in parallel with each other.

The cell treatment device according to the thirteenth aspect is capable of arranging the through holes on the slit member at high densities.

Fourteenth Aspect

A fourteenth aspect of the invention is directed to the cell treatment device according to first to thirteenth aspects, wherein two of the slit members are provided and the two slit members are arranged so that the first surfaces face each other.

The cell treatment device according to the fourteenth aspect is configured to supply the cell dispersion liquid to the first surface sides of the two slit members simultaneously. Accordingly the cell treatment device is further downsized.

Fifteenth Aspect

A fifteenth aspect of the invention is directed to a cell treatment cartridge which allows cell dispersion liquid including cancer cells to pass therethrough to cause at least the cancer cells to be subjected to at least one of a physical action, a chemical action, and a biologically activating action, including: a slit member having a first surface and a second surface and including a through hole having a slit shape penetrating from the first surface to the second surface and extending in one direction, the through hole having a tapered portion, the width of a cross section of the tapered portion orthogonal in the one direction reduces from the first surface toward the second surface side, and is smaller than an average diameter of the cancer cells at an end on the second surfaces side, and the cell dispersion liquid is allowed to pass from the first surface side through the through hole to the second surface side.

The cell treatment cartridge according to the fifteenth aspect is capable of causing at least one of the cancer cells and immune cells to be subjected to at least one of the physical action, the chemical action, and the biologically activating action by allowing cell dispersion liquid including at least one of the cancer cells and the immune cells to pass therethrough.

Sixteenth Aspect

A sixteenth aspect of the invention is directed to a body fluid treatment system using a cell treatment device or a cell treatment cartridge, which allows cell dispersion liquid including cancer cells to pass therethrough to cause at least the cancer cells to be subjected to at least one of a physical action, a chemical action, and a biologically activating action, including: a slit member having a first surface and a second surface and including a through hole having a slit shape penetrating from the first surface to the second surface and extending in one direction, the through hole having a tapered portion, in which the width of a cross section of the tapered portion orthogonal in the one direction reduces from the first surface toward the second surface side, and is smaller than an average diameter of the cancer cells at an end on the second surfaces side, and the cell dispersion liquid is allowed to pass from the first surface side through the through hole to the second surface side.

The body fluid treatment system according to the sixteenth aspect is capable of causing at least one of the cancer cells and immune cells to be subjected to at least one of the physical action, the chemical action, and the biologically activating action by allowing the body fluid including at least one of the cancer cell and the immune cells to pass therethrough.

BRIEF DESCRIPTION OF THE DRAWINGS

The invention will be described with reference to the accompanying drawings, wherein like numbers reference like elements.

DESCRIPTION OF EXEMPLARY EMBODIMENTS

Figure 1:
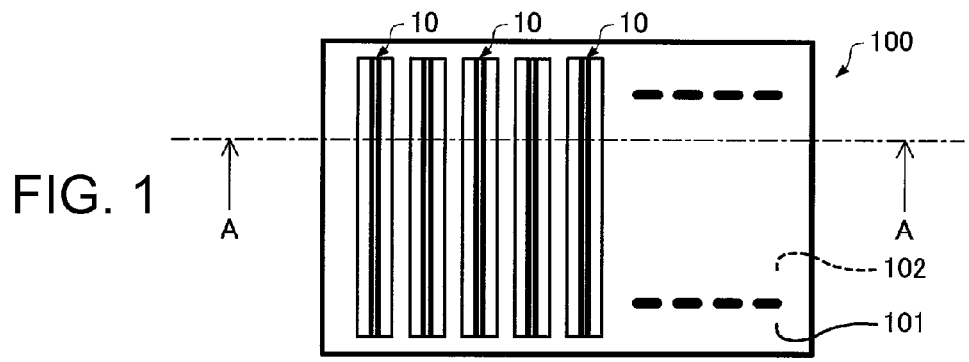
FIG. 1 is a plan view diagrammatically showing a slit member according to an embodiment.

Referring now to the drawings, a preferred embodiment of the invention will be described. The embodiment described below is intended to explain an example of the invention.

1. Cell Treatment Device

A cell treatment device according to the embodiment is configured to subject cancer cells to at least one of a physical action, a chemical action, and a biologically activating action by allowing cell dispersion liquid including the cancer cells to pass therethrough.

1.1. Cell Dispersion Liquid

The cell treatment device according to the embodiment allows cell dispersion liquid to pass therethrough. As the cell dispersion liquid, for example, body fluid of animals such as human beings, that is, blood, lymph fluid, tissue fluid, celomic fluid, and the like are exemplified. Also, the cell dispersion liquid according to the embodiment is not limited to biological-originated fluid, and may be cell dispersion material prepared by dispersing cells therein artificially for tests, studies or the like.

The cell dispersion liquid which is passed through the cell treatment device according to the embodiment includes cancer cells. The cell dispersion liquid may include cells other than cancer cells dispersed therein. For example, the cell dispersion liquid may include immune cells. For example, the cell dispersion liquid may include cells such as white blood cells (immune cells), red blood cells, blood platelets, and the like dispersed therein in addition to the cancer cells such as blood.

In this specification, the term "cancer cells" means cells which constitute cancer (malignant tumor). Cancer has a characteristic to cause metastasis, and the cancer cells are mixed to the body fluid such as blood or the like described above at the time of metastasis of the cancer. The cancer cells which are mixed in the blood and hence are brought into a state of being capable of circulating in a living body through a blood vessel are referred to as a circulating cancer cell (CTC: Circulating Tumor Cell). Therefore, the cell dispersion liquid which passes through the cell treatment device according to the embodiment may be blood including the circulating cancer cells. In this specification, the term "immune cells" means cells such as white blood cells, that is, blood granulocytic cells, lymph cells, monocytes, and the like.

1.2. Physical Action, Chemical Action, and Biologically Activating Action

The cell treatment device according to the embodiment is configured to subject at least cancer cells to at least one of the physical action, the chemical action, and the biologically activating action.

The term "physical action" means contact, trap, adhesion, adsorption, crushing, and the like. The term "physical action" in this specification includes, for example, trapping cancer cells in through holes (described later), and bringing the cancer cells and the immune cells into contact with a slit member. Furthermore, the physical action also includes elongating staying time of the cells in the cell treatment device when the cells pass through the cell treatment device.

The chemical action indicates causing the functions of the cancer cells to change by a chemical substance such as medical agent or the like. As the chemical action, for example, changing the functions of cancer cells by contact between molecules of the anti-cancer agent or the like and the cancer cells is exemplified.

The term "biologically activating action" means providing biologically active information to cancer cells or immune cells and causing necrosis, growth, multiplication, activation, protein synthesis acceleration, and growth restrain thereof.

The biologically activating action includes, for example, bringing cancer cells into apoptosis, bringing cancer cells into necrosis, activating immune cells, and multiplying immune cells, and so on. In this specifically, an action for discriminating cells such that antibodies bind to antigens possessed by cancer cells is included in the biologically activating action.

1.3. Structure of Cell Treatment Device

The cell treatment device according to the embodiment includes a slit member formed with through holes 10.

1.3.1. Slit Member

The slit member is a member which constitutes a principal portion of the cell treatment device in the embodiment. The slit member is not specifically limited as long as the through holes 10, described later, are formed. A slit member 100 and a slit member 200 exemplified below have contours of a flat-panel shape and a cylindrical shape, respectively. Both of these slit members function desirably as the principal portion of the cell treatment device in the embodiment. The contour of the slit member is not limited to the flat-panel shape and the cylindrical shape.

Figure 2:
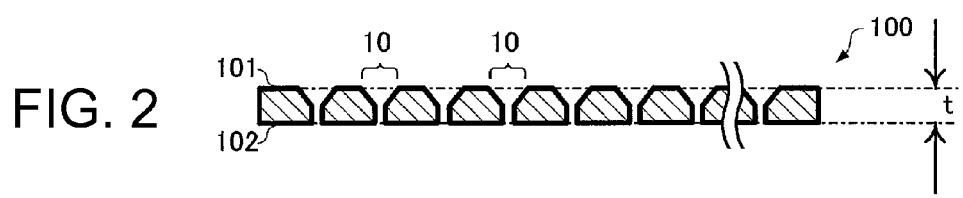
FIG. 2 is a diagrammatic drawing of a cross section of the slit member according to the embodiment.
Figure 3:
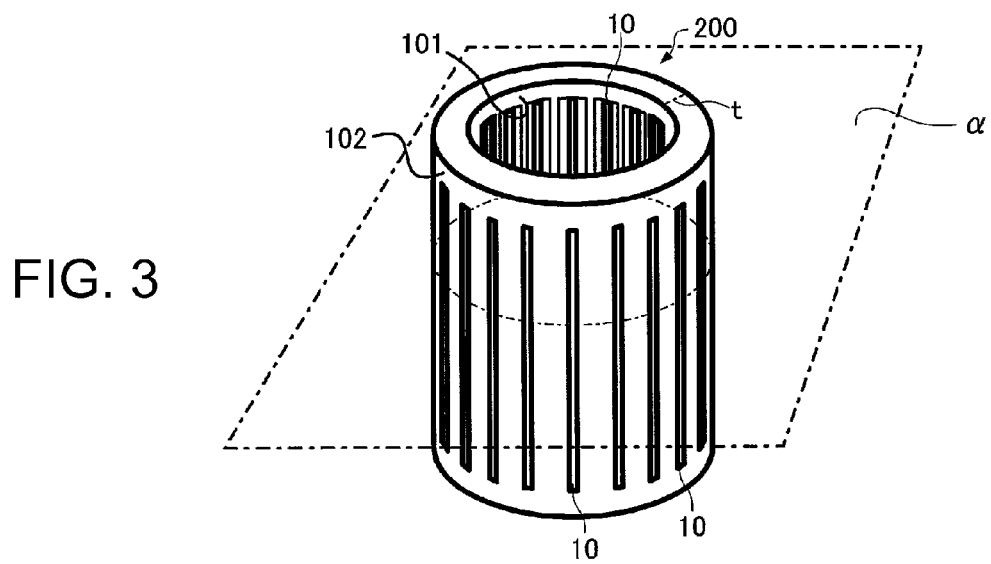
FIG. 3 is a perspective view diagrammatically showing a slit member according to an embodiment.
Figure 4:
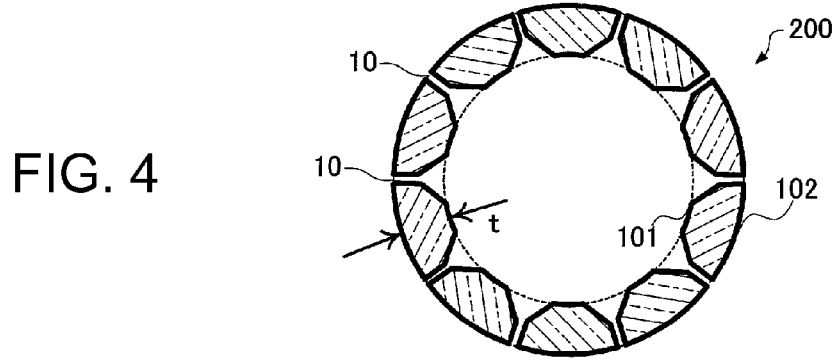
FIG. 4 is a diagrammatic drawing of the slit member according to the embodiment.

FIG. 1 is a plan view diagrammatically showing the slit member 100 as a mode of the slit member. FIG. 2 is a diagrammatic drawing of a cross section of the slit member 100. A cross section taken along the line A-A in FIG. 1 corresponds to FIG. 2. FIG. 3 is a perspective view diagrammatically showing the slit member 200 as a mode of the slit member. FIG. 4 is a diagrammatic drawing of a cross section of the slit member 200. A cross section taken along a plane α in FIG. 3 corresponds to FIG. 4.

The slit member includes a first surface 101 and a second surface 102. In an example of the slit member 100 of a panel shape, a main surface on one side corresponds to the first surface 101 and the other main surface corresponds to the second surface 102. In an example of the slit member 200 of a cylindrical shape, an inner peripheral surface corresponds to the first surface 101 and an outer peripheral surface corresponds to the second surface 102. In the example of the slit member 200, a configuration in which the outer peripheral surface corresponds to the first surface 101 and the inner peripheral surface corresponds to the second surface 102 is also applicable.

The size and the shape of the slit member is not limited. For example, the flat shape of the slit member 100 may be a rectangular shape or a circular shape. In an example shown in FIG. 1, the flat shape of the slit member 100 is formed into a rectangular shape. In the cylindrical shape of the slit member 200, circles at both ends of the cylinder may have different sizes. In the example shown in FIG. 3, the circles at the both ends of the cylinder have the same size.

A thickness t of the slit member corresponds to the distance between the first surface 101 and the second surface 102. The thickness t may be designed according to the functions of the through holes 10 described later. The thickness t of the slit member may fall in a range, for example, from 1 μm to 100 mm inclusive. When the thickness t of the slit member is 1 μm or smaller, the strength of a cell treatment device 1000 might be insufficient. The upper limit of the thickness t of the slit member is not specifically limited. However, if the thickness t is too large, the cell treatment device may be upsized or the resistance generated when the cell dispersion liquid passes therethrough may become too high.

The material of the slit member is not specifically limited. As the material of the slit member, inorganic materials and organic materials are exemplified and, for example, metallic materials such as stainless steel, chrome-cobalt alloy, oxide materials, ceramics materials, semiconductor materials such as silicon, polysulfone, polyether sulfone, polyester-based resin, ethylene-vinylalcohol copolymer, polymethylmethacrylate, polyurethane, polyacrylonitrile copolymer, polyamide, polyimide, silicone resin, fluorine contained resins such as polytetrafluoroethylene (PTFE), and polymer molecule materials such as alloys of these materials, cellulose-based materials such as regenerated cellulose, surface modified regenerated cellulose, cellulose acetate based substances, and so on.

The slit member is preferably formed of a material which is high in biocompatibility. As the biocompatible materials, for example, polysulfone, polyether sulfone, polyester-based resin, ethylene-vinylalcohol copolymer, polymethylmethacrylate, polyacrylonitrile copolymer, cellulose-based materials, and fluorine contained resins such as polytetrafluoroethylene (PTFE) are exemplified from among those described above. When the slit member is formed of a material having biocompatibility, for example, toxicity with respect to cells in cell dispersion liquid may be restrained and, when immune cells are contained in the cell dispersion liquid, the immune cells and the like are prevented from recognizing the slit member as a foreign substance. In addition, when the cell dispersion liquid is blood, if the biocompatible material is selected as the material of the slit member, a blood coagulating action is restrained. When the slit member is formed of a material which has low biocompatibility, the surface of the slit member may be coated with a biocompatible material. As the coating, a coating having at least one of the functions selected from hydrophilic nature, water repellency, and blocking tendency is exemplified. By the application of the coating as described above, cells are prevented from sticking nonspecifically fast to the surface of the slit member when the cell dispersion liquid passes through the slit member. Accordingly, for example, the resistance generated when the cell dispersion liquid passes therethrough may be restrained. In addition, for example, in a case where the cell dispersion liquid is blood, cells other than the cancer cells and immune cells are restrained from sticking nonspecifically fast to the surface of the slit member, so that clogging of the cell treatment device is restrained.

As a function of the slit member, formation of the through holes 10 is exemplified. The cell dispersion liquid passes from the first surface 101 side of the slit member through the through holes 10 to the second surface 102 side. The number of the through holes 10 formed on the slit member is not limited. When the number of the through holes 10 is increased, the flow rate of the cell dispersion liquid may be increased correspondingly.

A mode of the through holes 10 will be exemplified below. In a case where a plurality of the through holes 10 are formed on the slit member, the through holes 10 may have different forms, or may have the same form.

1.3.2. Through Hole

The through holes 10 penetrate through the slit member from the first surface 101 to the second surface 102, and each have a slit shape extending in one direction. The through holes 10 penetrate through the slit member in the direction of the thickness t. The through holes 10 connect the first surface 101 and the second surface 102 by penetrating through the slit member from the first surface 101 to the second surface 102.

The term "slit shape" means the shape of a hole penetrating thorough a plate-shaped substance and a hole extending longitudinally in a specific direction when viewing the substance in plan view. The direction of extension of the through hole 10 into the slit shape is not specifically limited. For example, in the example of the slit member 100 described above, the through holes 10 may each have a shape elongated in a direction along one side of the contour of the rectangular shape in plan view as shown in FIG. 1. Also, in the example of the slit member 200, the through holes 10 may each have a shape elongated in a direction along a center axis of the cylinder as shown in FIG. 3. One end of each of the through holes 10 viewed in plan view may be connected to an outer periphery of the slit member. In other words, the through holes 10 may be of a state of notches formed on the slit member. In addition, both ends of each of the through holes 10 viewed in plan view may be connected to the outer periphery of the slit member. In other words, the through holes 10 may be of a state of disconnecting the slit member. When the through holes 10 are connected to the outer periphery of the slit member, for example, the through holes 10 may be formed by connecting a flow channel forming member described later to the slit member. When the length of the through holes 10 in the extending direction is increased, the flow rate of the cell dispersion liquid may be increased.

FIG. 5 to FIG. 11 are diagrammatic drawings of cross sections of the slit member for explaining the through hole 10. As described above, the first surface 101 and the second surface 102 of the slit member may be any of a flat surface and a curved surface. However, in the description of the through hole 10 given below, the first surface 101 and the second surface 102 are assumed to be flat surfaces parallel to each other. Although, the number of the through holes 10 formed on the slit member is not limited as described above, in the following description, one of the through holes 10 will be described. In this specification, the width of respective portions of the through hole 10 is defined in a cross section orthogonal to the direction of extension of the through hole 10 (for example, the cross section shown in FIG. 5 to FIG. 11).

The through hole 10 includes a tapered portion 12. The tapered portion 12 constitutes part or entire part of the through hole 10. The tapered portion 12 includes a portion of the through hole 10 connected to the first surface 101 of the slit member. The surface of the slit member which forms the tapered portion 12 may be referred to as a tapered surface 112 hereinafter. The tapered surface 112 is connected at least to the first surface 101 of the slit member.

Figure 5:
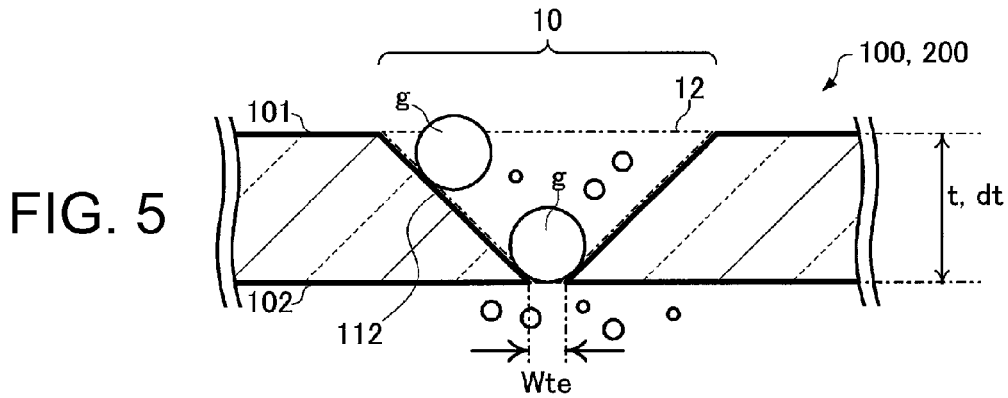
FIG. 5 is a diagrammatic drawing of a cross section of the slit member according to the embodiment.

The width of the tapered portion 12 is reduced from the first surface 101 toward the second surface 102 as shown in FIG. 5. In an example shown in FIG. 5, the width of the tapered portion 12 is reduced monotonously from the first surface 101 toward the second surface 102. The degree of reduction of the width of the tapered portion 12, that is, the inclination of the tapered surface 112 with respect to the first surface 101 and the second surface 102 is not limited. In the example shown in FIG. 5, the cross section of the tapered surface 112 is linear. However, it may be a polygonal line or a curved line. In a case where the slit member has a plurality of the through holes 10 and where the tapered portions 12 of the adjacent through holes 10 are in contact with each other, the flat portion of the first surface 101 does not exist. In such a case, a virtual plane which defines the thickness t of the slit member may be regarded as the first surface 101 (for example, see FIG. 15).

The width of the tapered portion 12 is smaller than an average diameter of a cancer cell at an end of the second surface 102 side. The width of the portion of the tapered portion 12 other than the end on the side of the second surface 102 is not limited as long as it is reduced from the first surface 101 toward the second surface 102. In the example shown in FIG. 5, a width Wte of the tapered portion 12 at the end on the side of the second surface 102 is smaller than that of a cancer cell.

The average diameter of cancer cells is reported as follows. The circulating cancer cells are larger in average diameter than normal cells in blood (for example, American Journal of Pathology, Vol. 156, No. 1, 57-63, January 2000).

In this report, light-optic micrographs of a plurality of types of circulating cancer cells are taken. Then, according to the report, an average projection area of the variety of circulating cancer cells was from 396 $\mu m^2$ to 796 $\mu m^2$ inclusive. Therefore, assuming that the shape of the variety of the circulating cancer cells is a spherical shape, the average diameter of the circulating cancer cells in the cited reference described above was found to be from 22 μm to 32 μm inclusive.

For example, when the circulating cancer cells having an average diameter of 22 μm in the cited reference described above are included in the cell dispersion liquid, the width Wte of the tapered portion 12 at the end of the second surface 102 side is 22 μm or smaller. In the same manner, when the circulating cancer cells having an average diameter of 32 μm in the cited reference described above are included in the cell dispersion liquid, the width Wte of the tapered portion 12 at the end of the second surface 102 side is 32 μm or smaller.

In this manner, the width Wte of the tapered portion 12 of the through hole 10 of the slit member at the end of the second surface 102 side may be selected specifically within the range described above according to the type of the treatment of the cell dispersion liquid.

The size (depth dt) in the direction of the thickness t of the slit member of the tapered portion 12 is not limited. The depth dt of the tapered portion 12 with respect to the thickness t of the slit member may be from 1% to 100% inclusive. In the example shown in FIG. 5, the depth dt of the tapered portion 12 is the same (100%) as the thickness t of the slit member.

In FIG. 5, cancer cells and other cells are diagrammatically illustrated. Although described above, the cell dispersion liquid passes through the slit member from the first surface 101 side to the second surface 102 side. In the example shown in FIG. 5, the cell dispersion liquid passes from the top to the bottom. The cell dispersion liquid includes cancer cells g. Since the slit member has the tapered portion 12 described above, the physical action to bring the cancer cells g into contact with the slit member at least at the end of the tapered portion 12 on the second surface 102 side is achieved as shown in FIG. 5. For example, when a biologically active substance is fixed to the tapered surface 112, the cancer cells are subjected to the biologically activating action efficiently.

The cancer cell g which comes into contact with the end of the tapered portion 12 on the second surface 102 side as described above cannot pass through the through hole 10 unless otherwise deformed. Therefore, the slit member is capable of applying at least the physical action as "trapping" to the cancer cells g which can hardly be deformed. Accordingly, the cancer cells in the cell dispersion liquid can be removed or reduced. As shown in FIG. 5, when the end of the tapered portion 12 on the second surface 102 side connects to the second surface 102 and has a sharp state, the cancer cell g which comes into contact therewith is subjected to the physical action such as destroying a cell surface membrane.

In contrast, when the cells having diameters smaller than cancer cells are included in the cell dispersion liquid, such cells are not trapped by the slit member and pass through the cell treatment device. For example, when the cell dispersion liquid is blood including circulating cancer cells, red blood cells and blood platelets are not trapped by the slit member, and may pass through the cell treatment device.

In a case where a cancer cell tries to pass through the through hole 10 by changing the shape, the staying time of the cancer cell in the cell treatment device during passage of the cell dispersion liquid may be elongated than other cells. Therefore, when the cell treatment device is irradiated with a radioactive ray such as visible light, UV light, X-rays, gamma rays, corpuscular rays, and so on, the irradiation time with respect to the cancer cells can be set to be longer than to other cells. In this case, a material which allows easy transmission of the radioactive ray therethrough is selected as the material of the cell treatment device.

Since the through hole 10 has the slit shape, if a cancer cell is collected or trapped at part of the through hole 10, the remaining portion still functions as the through hole 10 sufficiently. In other words, since the through hole 10 has a slit-type shape, it is hardly be clogged even after having trapped the cancer cell, and hence a flow channel for the cell dispersion liquid is sufficiently secured. When the cell dispersion liquid is blood and includes circulating cancer cells therein, the number of the circulating cancer cells is much smaller than the number of blood cells in the blood. For example, it is said that the number of circulating cancer cells in blood of a cancer patient is on the order of zero to ten in 7.5 ml of blood, and the number of the circulating cancer cells is approximately a 40 billionth to a 4 billionth part of the number of blood cells. Therefore, for example, when the cell dispersion liquid is blood, clogging hardly occurs in the cell treatment device in the embodiment.

1.3.3. Modification of Through Hole

Figure 6:
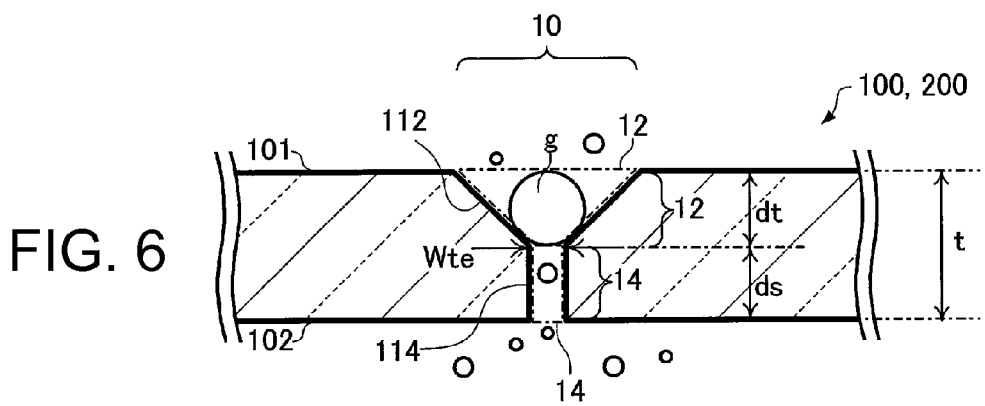
FIG. 6 is a diagrammatic drawing of a cross section of the slit member according to the embodiment.
Figure 7:
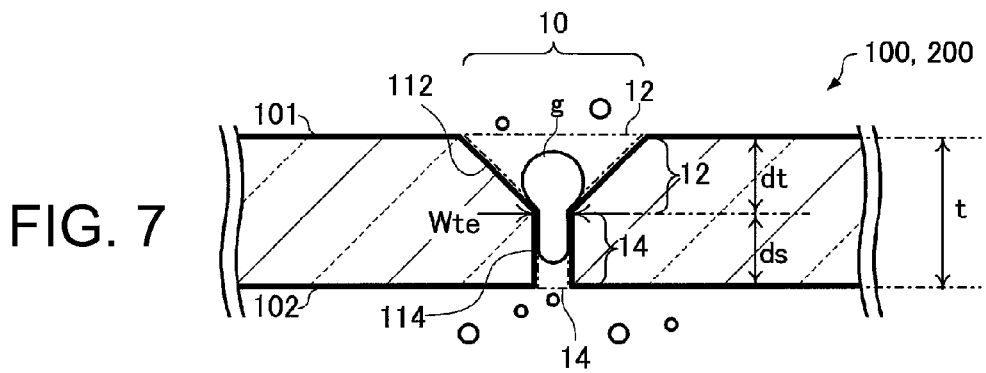
FIG. 7 is a diagrammatic drawing of a cross section of the slit member according to the embodiment.

The through hole 10 may have a narrowed portion 14. FIG. 6 and FIG. 7 are diagrammatic drawings of cross sections of the slit member when the through hole 10 has the narrowed portion 14.

The narrowed portion 14 is formed continuously at the end of the tapered portion 12 on the second surface 102 side. The narrowed portion 14 is part of the through hole 10. The narrowed portion 14 continues to the tapered portion 12 of the through hole 10, and is positioned on the second surface 102 side with respect to the tapered portion 12. The surface of the slit member which forms the narrowed portion 14 may be referred to as a narrowed surface 114, hereinafter. The narrowed surface 114 continues to the tapered surface 112. The narrowed surface 114 may be connected to the second surface 102 of the slit member. The narrowed surface 114 may be connected to the second surface 102, for example, via an inverted tapered surface 116 (described later). In the examples shown in FIG. 6 and FIG. 7, the narrowed portion 14 connects the end of the tapered portion 12 on the second surface 102 side and the second surface 102 of the slit member.

The size (depth ds) in the direction of the thickness t of the slit member of the narrowed portion 14 is not limited. The depth ds of the narrowed portion 14 with respect to the thickness t of the slit member may be from 0% to 99% inclusive. In an example shown in FIG. 6, the depth ds of the tapered portion 12 is about 50% of the thickness t of the slit member. In the same drawings, the depth dt of the tapered portion 12 is about 50% of the thickness t of the slit member.

The width of the narrowed portion 14 is equal to or smaller than the width Wte at the end of the tapered portion 12 on the second surface 102 side. Therefore, the width of the narrowed portion 14 is smaller than the average diameter of cancer cells. In the examples shown in FIG. 6 and FIG. 7, the narrowed portion 14 is formed to have a constant width (the width Wte at the end of the tapered portion 12 on the second surface 102 side).

With the formation of the narrowed portion 14 as described above, the following effects are achieved. Cancer cells include those having flexibility in shape depending on the types. As shown in FIG. 7, the formation of the narrowed portion 14 makes passage of the cancer cell g which tries to pass therethrough by changing the shape difficult when the cell dispersion liquid passes therethrough. Accordingly, the physical action such as trapping the cancer cell g may be enhanced. As shown in FIG. 7, the formation of the narrowed portion 14 enlarges the contact surface area of the cancer cell g trying to pass therethrough by changing the shape with respect to the surface of the slit member. Accordingly, for example, when a biologically active substance is fixed to the narrowed surface 114, the cancer cells are subjected to the biologically activating action further reliably. When the narrowed portion 14 is formed, a thin portion in shape of the tapered portion 12 on the second surface 102 side is reduced. Therefore, the mechanical strength of the slit member can be enhanced.

The width of the narrowed portion 14 can be changed in the direction of the thickness t of the slit member. For example, the width of the narrowed portion 14 may be set into multisteps corresponding to the size of cells included in the cell dispersion liquid.

Figure 8:
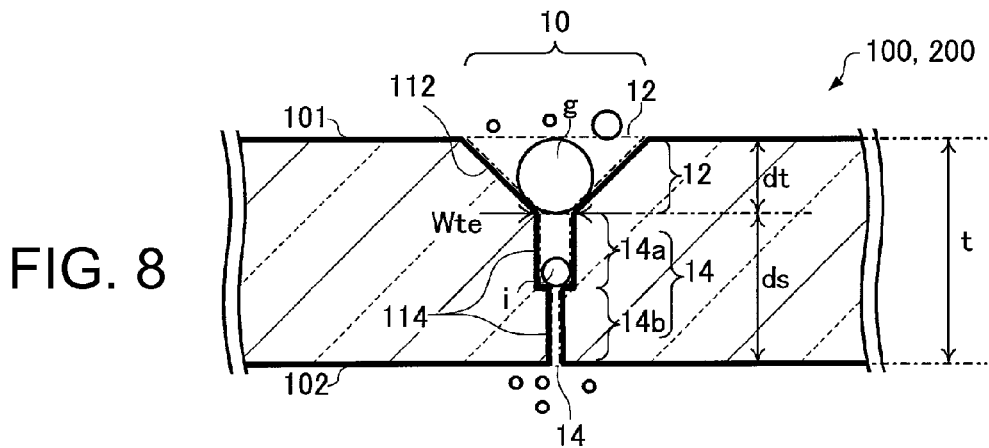
FIG. 8 is a diagrammatic drawing of a cross section of the slit member according to the embodiment.

FIG. 8 is a diagrammatic drawing of a cross section of the slit member where the narrowed portion 14 has the multistep width. The narrowed portion 14 may have a first area 14a on the first surface 101 side and a second area 14b on the second surface 102 side as shown in FIG. 8. Then, the width of the second area 14b is smaller than the width of the first area 14a, and is smaller than the average diameter of immune cells.

In general, it is said that the average diameter of the immune cells is 20 μm or smaller. In other words, from among white blood cells as immune cells, it is said that the diameters of blood granulocytic cells are from 12 μm to 15 μm inclusive for neutrophilic cells, from 13 μm to 20 μm inclusive for acidophilic cells, and from 10 μm to 16 μm inclusive for basophilic cells, the diameters of monocytes (macrophage, dendritic cells) are from 15 μm to 20 μm inclusive, and the diameters of lymph cells (T cells, suppressor T cells, B cells, NK cells, and NKT cells) are from 7 μm to 10 μm inclusive.

For example, it is also possible to reduce the width of the second area 14b to a value smaller than the average diameter of immune cells by forming the first area 14a and the second area 14b in the narrowed portion 14. For example, when setting the width of the narrowed portion 14 into multisteps, the width of the first area 14a may be set to the width Wte at the end of the tapered portion 12 on the second surface 102 side and the width of the second area 14b may be set to a value from 7 μm to 20 μm inclusive.

In this configuration, the second area 14b has a smaller width than immune cells. Therefore, when immune cells are included in the cell dispersion liquid, the immune cells may come into contact with the narrowed surface 114 in the second area 14b at a high frequency. For example, when a biologically active substance is fixed to the narrowed surface 114, the immune cells are efficiently subjected to the biologically activating action. By setting the width of the narrowed portion 14 into multisteps, a plurality of effects may be applied to a plurality of types of cells in the cell dispersion liquid by a single passage. For example, the first area 14a may allow cancer cells to be trapped, and the second area 14b may allow immune cells to be subjected to the chemical action, the biologically activating action, and the like efficiently.

Figure 9:
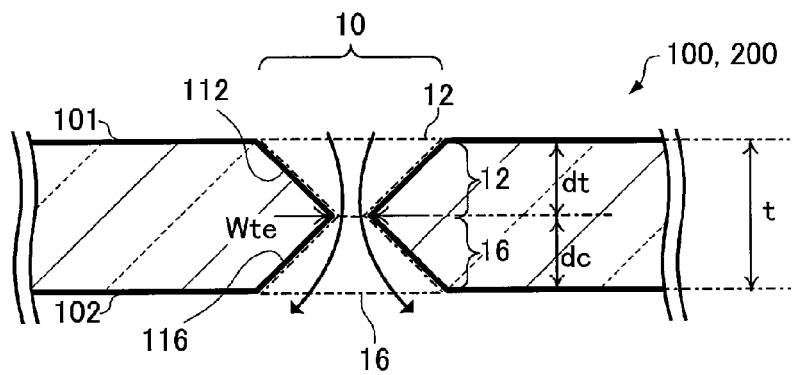
FIG. 9 is a diagrammatic drawing of a cross section of the slit member according to the embodiment.
Figure 10:
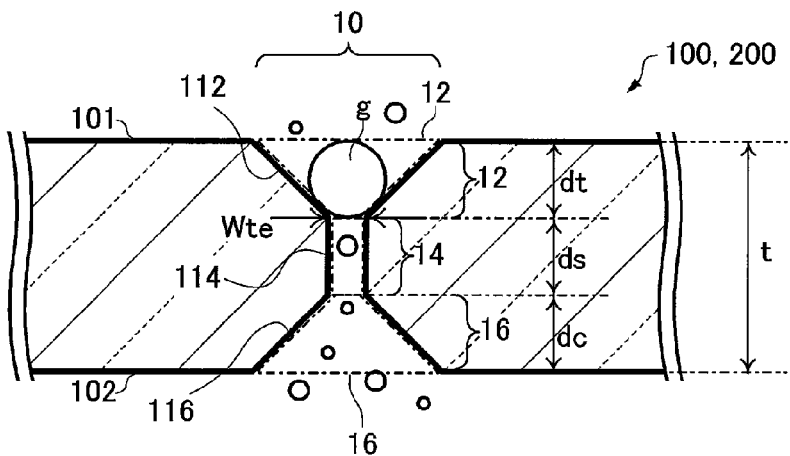
FIG. 10 is a diagrammatic drawing of a cross section of the slit member according to the embodiment.

The through hole 10 may have an inverted tapered portion 16. FIG. 9 and FIG. 10 are diagrammatic drawings of cross sections of the slit member when the through hole 10 has the inverted tapered portion 16.

The inverted tapered portion 16 is formed continuously at the end of the tapered portion 12 on the second surface 102 side, or at the end of the narrowed portion 14 on the second surface 102 side. The inverted tapered portion 16 is formed at a position of the through hole 10 connected to the second surface 102 side of the slit member. The surface of the slit member which forms the inverted tapered portion 16 may be referred to as an inverted tapered surface 116 hereinafter. The inverted tapered surface 116 continues to the tapered surface 112 or the narrowed surface 114. The inverted tapered surface 116 may be connected to the second surface 102 of the slit member. In an example shown in FIG. 9, the inverted tapered portion 16 connects the end of the tapered portion 12 on the second surface 102 side and the second surface 102 of the slit member. In an example shown in FIG. 10, the inverted tapered portion 16 connects the end of the narrowed portion 14 on the second surface 102 side and the second surface 102 of the slit member.

The size (depth dc) in the direction of the thickness t of the slit member of the inverted tapered portion 16 is not limited. The depth do of the inverted tapered portion 16 with respect to the thickness t of the slit member may be from 0% to 99% inclusive. In the example shown in FIG. 9, the depth dc of the inverted tapered portion 16 is about 50% of the thickness t of the slit member. In the same drawings, the depth dt of the tapered portion 12 is about 50% of the thickness t of the slit member. In the example shown in FIG. 10, the depth dc of the inverted tapered portion 16 is about one-third of the thickness t of the slit member. In the same drawings, the depth dt of the tapered portion 12 is about one-third of the thickness t of the slit member, and the remaining one-third corresponds to the narrowed portion 14.

The width of the inverted tapered portion 16 is increased from the first surface 101 side toward the second surface 102. The width of the inverted tapered portion 16 is, in the examples shown in FIG. 9 and FIG. 10, increased monotonously from the first surface 101 side toward the second surface 102. The degree of increase of the width of the inverted tapered portion 16, that is, the inclination of the inverted tapered surface 116 with respect to the first surface 101 and the second surface 102 is not limited. In the examples shown in FIG. 9 and FIG. 10, the cross section of the inverted tapered surface 116 is linear. However, it may be a polygonal line or a curved line.

The inverted tapered portion 16 is connected to the narrowed portion 14 or the tapered portion 12 on the first surface side. Therefore, the width of the inverted tapered portion 16 is smaller than an average diameter of a cancer cell at an end of the first surface 101 side. The width of the portion of the inverted tapered portion 16 other than the end on the side of the first surface 101 is not limited as long as it is increased from the first surface 101 side toward the second surface 102. In the examples shown in FIG. 9 and FIG. 10, the width of the inverted tapered portion 16 at the end on the first surface 101 side is equal to the width Wte of the tapered portion 12 on the second surface 102 side and is smaller than that of a cancer cell.

Figure 11:
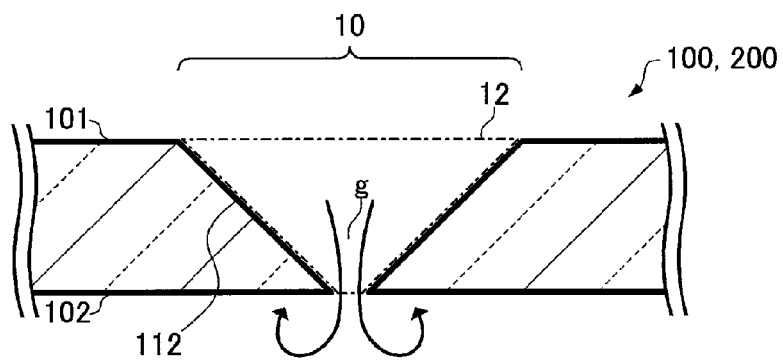
FIG. 11 is a diagrammatic drawing of a cross section of the slit member according to the embodiment.

With the formation of the inverted tapered portion 16 as described above, the following effects are achieved. FIG. 11 illustrates an arrow diagrammatically showing a state of flow of the cell dispersion liquid in a case where the through hole 10 does not have the inverted tapered portion 16. FIG. 9 illustrates an arrow diagrammatically showing a state of flow of the cell dispersion liquid in a case where the through hole 10 has the inverted tapered portion 16. When the through hole 10 does not have the inverted tapered portion 16, as shown in FIG. 11, there may be a case where a whirl (eddy current) of the cell dispersion liquid as shown in the second surface 102 side of the slit member is generated. When such the whirl is generated, retention of the cell dispersion liquid may occur. When the retention occurs, if the cell dispersion liquid is blood, coagulation of blood or thrombus may occur at a portion of the retention. When the through hole 10 has the inverted tapered portion 16, the whirl or the like of the cell dispersion liquid is restrained, and the state of flow may be stabilized as shown in FIG. 9. Therefore, if the cell dispersion liquid is blood, coagulation of blood or the like due to the retention may be restrained.

Figure 12:
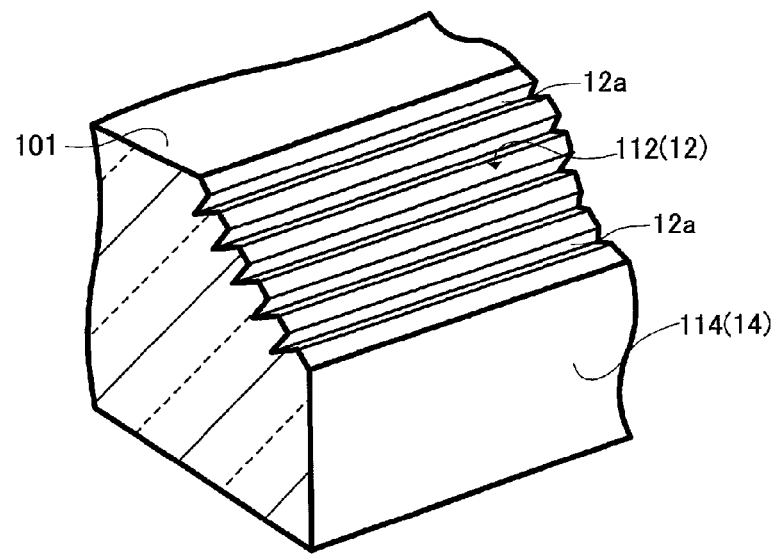
FIG. 12 is a perspective view diagrammatically showing a principal portion of the slit member according to an embodiment.
Figure 13:
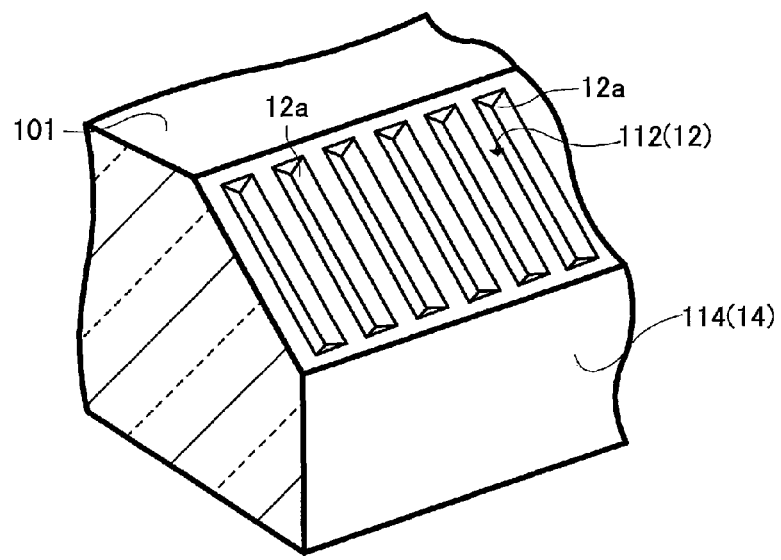
FIG. 13 is a perspective view diagrammatically showing a principal portion of the slit member according to an embodiment.

The through hole 10 may have projections and depressions on the tapered portion 12. In other words, the tapered surface 112 of the slit member may be formed with grooves 12a. None of the number, the depth, the shape, and the arrangement of the grooves 12a are not specifically limited, and may be of stripe patterns, grid patterns, and dot patterns, for example. FIG. 12 and FIG. 13 are perspective views diagrammatically showing principal portions of the slit member in which the grooves 12a are formed on the tapered surface 112. In the examples shown in FIG. 12 and FIG. 13, the plurality of grooves 12a are formed on the tapered surface 112 in a stripe pattern. In the example shown in FIG. 12, the grooves 12a are formed in parallel in the direction of extension of the through hole 10. In the example shown in FIG. 13, the grooves 12a are formed in a direction intersecting the direction of extension of the through hole 10. Although not illustrated, the grooves 12a may include those extending in parallel to the direction of extension of the through hole 10 and those extending in the direction intersecting the direction of extension of the through hole 10.

When the grooves 12a are formed on the tapered surface 112, the surface area of the tapered surface 112 may be increased. Accordingly, cells in the cell dispersion liquid may have more opportunities to come into contact with the tapered surface 112. When the grooves 12a are formed on the tapered surface 112, the state of flow of the cell dispersion liquid may be varied. For example, when the cell dispersion liquid passes through the tapered portion 12, if the grooves 12a are not formed, the cell dispersion liquid may pass through in a state similar to a laminar flow having less turbulence. With the formation of the grooves 12a, the turbulence may be generated when the cell dispersion liquid passes through the tapered portion 12, so that the flow of the cell dispersion liquid may be made to a further turbulent flow. Accordingly, cells passing through the tapered portion 12 may be brought into contact with the tapered surface 112 easily. Therefore, when a medical agent or a biologically active substance is fixed to the tapered portion 12 for example, cells in the cell dispersion liquid may be easily subjected to the chemical action, the biologically activating action, and the like.

1.3.4. Surface Modification

The cell treatment device in the embodiment is formed in such a manner that the width of the tapered portion 12 of the through hole 10 at the end on the second surface 102 side is smaller than the average diameter of cancer cells in the cell dispersion liquid. Therefore, the cancer cells come into contact with the surface of the slit member which forms the end of the tapered portion 12 on the second surface 102 side when the cell dispersion liquid passes through the cell treatment device. Therefore, by fixing at least one of a chemical substance and a biologically active substance which act on cancer cells on the surface of the slit member which forms at least the end of the tapered portion 12 on the second surface 102 side, cancer cells in the cell dispersion liquid may be subjected to at least one of the chemical action and the biologically activating action quite efficiently.

The cell dispersion liquid comes into contact also with portions which constitute the cell treatment device other than the slit member. In such the portion as well, by fixing at least one of a chemical substance and a biologically active substance, cancer cells in the cell dispersion liquid may be subjected to at least one of the chemical action and the biologically activating action. Also, surface modifications described below may provide multiplier effects by combining a plurality of modifications.

1.3.4.1. Cytokines

A Cytokine may be fixed to the surface of the slit member. The cytokines are substances which are in charge of information transfer between cells. As information to be transferred by the cytokines, for example, information which makes cells cause the biologically activating actions such as necrosis, growth, multiplication, activation, protein synthesis acceleration, and growth restrain is exemplified. The classification of the cytokines includes those based on functional changes occurring in cells which have received information transferred by the cytokines. For example, an apoptosis factor brings cancer cells into apoptosis (apoptosis inducing activation), and an immune cell activating factor is the cytokine which has information to activate the immune cells. In this specification, the cytokines may be referred to simply as the apoptosis factor, the immune cell activating factor, or the like. The cytokines include those acting specifically to specific cells and those acting non-specifically irrespective of the type of the cells.

As detailed examples of the apoptosis factor, a tumor necrosis factor) (TNF-$\alpha$, TNF-$\gamma$ and the like), TRAIL, FasL, lymphotoxin, non-cyclic retinoid, bikunin, parasporin, mitomycin, Taxol, Adiponectin, and so on are exemplified.

As a detailed example of the immune cell activating factor, interleukin-2 (IL-2), interleukin 12 (IL-12), interferon (IFN), TNF, and the like are exemplified. When immune cells come into contact with these immune cell activating factors, T cells or NK cells, for example, may be activated.

As a method of fixing a cytokine on the surface of the slit member, for example, a method of forming a self-organization monomolecular film (SAM) on the surface of the slit member and causing the cytokine to stick fast to or to bind to the SAM, a method of causing the cytokine to stick fast to or to bind to the surface of the slit member directly, and a method of synthesizing polymer molecules having the cytokine as a side chain or the like and applying the polymer molecules to the slit member are exemplified.

From among these methods, according to a method of causing the cytokine to stick fast to or to bind to the SAM, the cytokine may be arranged without irregularity, or with regularity and fixed. Therefore, the cytokine may be fixed on the surface of the slit member at high densities.

As an example of compound that forms the SAM, thiols, disulfides, alkoxysilanes, alkylsilanes, silane halide, and the like are exemplified. The SAM may be formed by causing these compounds to bind to the surface of the slit member as needed. At this time, the slit member may further be applied with the surface treatment or the like. For example, when a gold coat is applied to the surface of the slit member at a desired position, the SAM can be formed easily by thiols.

According to the method of applying a cytokine denatured polymer molecules having the cytokine as the side chain to the slit member, flexibility (fluctuation) of movement of the molecule of the cytokine is enhanced. For example, the cytokine denatured polymer molecules applied to the surface of the slit member is capable of causing a side chain constituting the molecule of the cytokine bound to each other to appear. Since such the side chain and a main chain to which the side chain is bound have maneuverability, flexibility is provided to the movement of the molecule of the cytokine in comparison with a case where the cytokine is fixed directly to the metal or the like. Therefore, the molecule of the cytokine is capable of moving within a certain spatial range. Accordingly, the opportunities of occurrence of contact between the cytokine and cancer cells may be increased. Also, since such the polymer molecules may be applied directly to the surface of the base material, it is easy to modify the surface. By using an inkjet printer as a device for applying such the polymer molecules, application to a selected arbitrarily minute area is enabled.

By the fixation of the cytokine to the surface of the slit member, cells which come into contact with the surface of the slit member may be subjected to the biologically activating action. Since the cytokine is fixed to the slit member, entry into the cell dispersion liquid is restrained. Then, when the cells having been acted upon by the chemical action or the biologically activating action by the cytokine have left the surface of the slit member and then other cells come into contact to the surface of the slit member, the other cells may be subjected to the same action. Accordingly, a number of cells may be subjected to the chemical action or the biologically activating action with a small amount of the cytokine.

In the slit member, the position where the cytokine is fixed is not specifically limited. However, the cytokine may demonstrate further remarkable effects by being fixed to the surface of the slit member which forms the end of the tapered portion 12 on the second surface 102 side. When the through hole 10 includes the tapered portion 12, further remarkable effects are obtained by fixing the cytokine on the tapered surface 112. For example, the apoptosis factors of cancer cells come into contact with the cancer cells reliably by being fixed to the narrowed surface 114 and, in addition, may be kept in contact therewith for a relatively long time (see FIG. 7). Accordingly, the cancer cells can be deadened further reliably.

Also, the immune cell activating factors come into contact with immune cells with high probabilities by being fixed to the narrowed surface 114. Accordingly, the immune cells are activated further efficiently. In addition, the immune cell activating factors come into contact with immune cells reliably by being fixed to the second area 14b in the case of the narrowed portion 14 having the multistep widths as described above. Accordingly, the immune cells are activated quite efficiently.

1.3.4.2. Antibody

An antibody may be fixed to the surface of the slit member. As a function of the antibody, binding to antigens is exemplified. As the antibody, antibodies which bind specifically to cancer antigens (saccharide, peptide, and the like) of cancer cells in the cell dispersion liquid may be used.

An antibody which binds specifically to a certain cancer antigen may be selected as needed according to the type of the cancer. As such the antibodies, for example, an anti-HER 2/neu used for mammary cancer, an NS19-9 antibody used for colon cancer, an anti-CD 25 antibody used for malignant B tumor, CD49, CD 54, CD59, and the like used for prostatic cancer are exemplified. The antibody to be fixed may be selected from antibodies which bind to a cancer antigen common to epithelial cancer. As such the antibodies, for example, Ep-CAM antibody, N-cadherin antibody, and the like are exemplified.

Fixation of the antibody on the surface of the slit member may be achieved in the same manner as the method of fixing the cytokine described in "1.3.4.1. Cytokines".

According to the method of causing the antibody to stick fast to or to bind to the SAM, arrangement and fixation of the antibodies without irregularity, or with regularity are achieved. Therefore, the antibody may be fixed on the surface of the slit member at high densities.

According to the method of applying antibody denatured polymer molecules having the antibody as the side chain to the slit member, flexibility (fluctuation) of movement of molecules of the antibodies is enhanced. For example, the antibody denatured polymer molecules applied to the surface of the slit member is capable of causing a side chain made up of molecules of the antibody bound to each other to appear. Since such the side chain and a main chain to which the side chain is bound have maneuverability, flexibility is provided to the movement of molecules of the antibody in comparison with a case where the antibody is fixed directly to the metal or the like. Therefore, the molecules of the antibody are capable of moving within a certain spatial range. Accordingly, the opportunities of occurrence of contact between the antibodies and cancer cells may be increased.

A method of fixing the Ep-CAM antibody on the surface of the slit member will be described below as an example.

An activating treatment (for example, plasma treatment) is applied in advance to the surface of the slit member according to the necessity. First of all, 1-ethyl-3-(3-dimethylaminopropyl) carbodiimide hydrochloride (EDC), N-Hydroxysuccinimide (NHS), and 2-(4-Morpholino)ethanesulfonic acid (MES), pH=6 (manufactured by Biotec Fisher GMBH), are added to physiologic saline buffer solution (manufactured by Sigma-Aldrich Corporation) to prepare intermediate forming solution.

Subsequently, the slit member is immersed in the intermediate forming solution to cause the same to react for approximately one hour to form succinimide ester intermediate on the surface of the slit member.

Subsequently, the intermediate forming solution is substituted hydrodynamically by anti-EpCAM monoclonal antibody (manufactured by R&D Systems) and PBS pH=7.4 (manufactured by Sigma-Aldrich Corporation), is left standstill for four hours for reaction, and then the anti-EpCAM antibody non-specifically stuck fast is washed off with PBS solution. For example, the Ep-CAM antibody can be fixed to the surface of the base material in the manner described above.

By the antibody being fixed to the surface of the slit member, the antibody binds to cancer antigens of cancer cells and, at least, is capable of causing the cancer cells to stay on the surface of the slit member. Therefore, the physical action to lower the velocity of the cancer cells passing through the cell treatment device is at least achieved by the antibody being fixed to the surface of the slit member. Also, since the antibody is fixed to the slit member, entry into the cell dispersion liquid is restrained. Then, when the cancer cells which are lowered in flow velocity due to the antibody have left the surface of the slit member, and then other cancer cells come into contact with the surface of the slit member again, the other cells are subjected to the same action. Accordingly, a number of cancer cells are subjected to the physical action with a small quantity of the antibody.

In the slit member, the position where the antibody is fixed is not specifically limited. However, the antibody may demonstrate further superior effects as described below by being fixed to the tapered surface 112. The trapped cancer cells come into contact with the tapered surface 112. However, when the antibody is fixed to the tapered surface 112, the action to trap the cancer cells is further enhanced. When the apoptosis factor or the like is fixed to the narrowed surface 114, if the antibody is fixed to the tapered surface 112, the cancer cells are kept in contact with the apoptosis factor for a longer time (see FIG. 7). Accordingly, the effect to deaden the cancer cells may further be enhanced.

Although the position to fix the antibody and the position to fix the apoptosis factor are described to be different positions in the example described above, the both may be fixed to the same position. In this configuration, for example, the apoptosis factor may be brought into contact with the cancer cells in a state in which the cancer cells are stationed by the antibody. Accordingly, the effect to cause the cancer cells to fall into apoptosis may be enhanced.

1.3.4.3. Ligand

A ligand may be fixed to the surface of the slit member. As a function of the ligand, binding to receptors possessed by cancer cells is exemplified. As the ligand, those which bind specifically to receptors possessed by cancer cells in the cell dispersion liquid are exemplified.

As a detailed example of the ligand, vitamins such as folic acid, saccharides such as galactose, polymer molecule compounds such as transferrin-Fe, and derivatives thereof are exemplified. In particular, when the cell dispersion liquid includes circulating cancer cells, folic acid receptors appear on the surfaces of the circulating cancer cells at a high frequency, so that the folic acid is preferably used as the ligand. Since the folic acid is a low polymer ligand, it is fixed to the surface of the slit member more tightly, so that the opportunities of occurrence of contact with the folic acid receptors may be increased.

Fixation of the ligand on the surface of the slit member may be achieved in the same manner as the method of fixing the cytokine described in "1.3.4.1. Cytokines".

According to the method of causing the antibody to stick fast to or to bind to the SAM, arrangement and fixation of the ligand without irregularity, or with regularity are achieved. Therefore, the ligand may be fixed on the surface of the slit member at high densities.

According to the method of applying ligand denatured polymer molecules having the ligand as the side chain or the like to the slit member, flexibility (fluctuation) of movement of molecules of the ligand is enhanced. For example, the ligand denatured polymer molecules applied to the surface of the slit member are capable of causing aside chain made up of molecules of the ligand bound to each other to appear. Since such the side chain and a main chain to which the side chain is bound have maneuverability, flexibility is provided to the movement of molecules of the ligand in comparison with a case where the ligand is fixed directly to the metal or the like. Therefore, the molecules of the ligand are capable of moving within a certain spatial range. Accordingly, the opportunities of occurrence of contact between the ligand and cancer cells may be increased.

As the effects obtained by the ligand being fixed to the surface of the slit member, causing cancer cells to stay on the surface of the slit member is exemplified. Therefore, at least the physical action to lower the velocity of passage of the cancer cells through the cell treatment device may be achieved. The ligand may be selected from low polymer ligands. When the low polymer ligand is fixed, the density of the ligand on the surface of the slit member may be enhanced, so that the action to trap cancer cells is enhanced.

In the slit member, the position where the ligand is fixed is not specifically limited. However, the ligand may demonstrate further superior effects as described below by being fixed to the tapered surface 112. The trapped cancer cells are adhered to the tapered surface 112. However, when the ligand is fixed to the tapered surface 112, the action to trap the cancer cells is further enhanced. When the apoptosis factor or the like is fixed to the narrowed surface 114, if the ligand is fixed to the tapered surface 112, the cancer cells are kept in contact with the apoptosis factor for a longer time. Accordingly, the effect to deaden the cancer cells may further be enhanced.

1.3.4.4. Others

Furthermore, peptides, saccharides, aptamers, and the like may be fixed to the surface of the slit member. As one of the functions of these compounds, for example, causing cancer cells to stay on the surface of the slit member by these compounds fixed to the surface of the slit member is exemplified. Therefore, at least the physical action to lower the velocity of passage of the cancer cells through the cell treatment device may be achieved. The position where these molecules are applied may be selected as needed according to the object in the same manner as the examples described above.

The modes of modification of the through hole 10 and the modes of the surface modifications described thus far may be applied independently or in combination to the cell treatment device according to the embodiment. When the plurality of modifications are combined to apply to the cell treatment device, there are combinations which achieve a multiplier effect in addition to the effects of the respective mode of modifications. In other words, by selecting the width of the through hole 10 and the function of the surface modification as needed, desired effects may be achieved efficiently with respect to target cells.

1.4. Flow Channel Forming Member

The cell treatment device according to the embodiment includes the slit member described above, and the slit member is formed with a flow channel for allowing the cell dispersion liquid to pass therethrough from the first surface 101 side to the second surface 102 side of the slit member. The shape of the flow channel and the configuration for forming the flow channel as such are not limited. Hereinafter, an example of formation of the flow channels using the flow channel forming member in a case of including the flat panel-shaped slit member 100 in the cell treatment device and in a case of including the cylindrical slit member 200 will be described.

Figure 14:
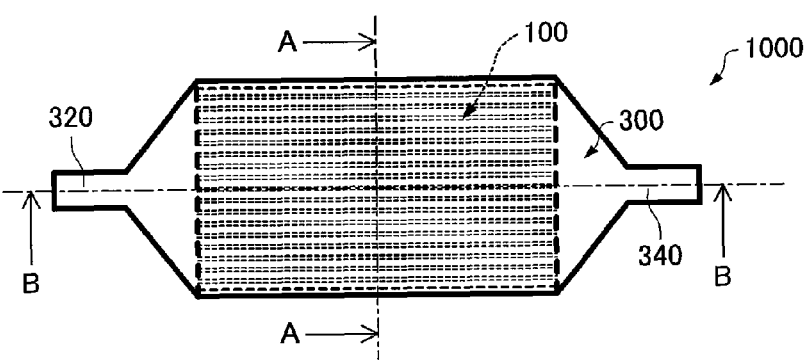
FIG. 14 is a plan view diagrammatically showing a cell treatment device according to an embodiment.
Figure 15:
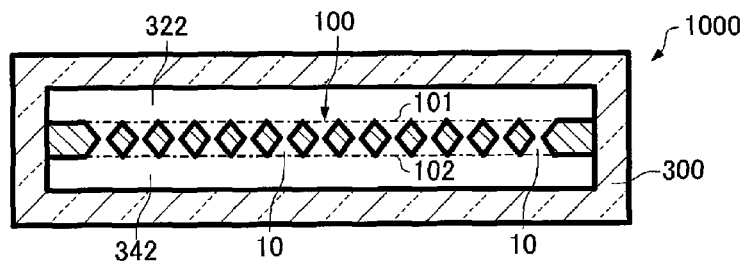
FIG. 15 is a diagrammatic drawing of a cross section of the cell treatment device according to the embodiment.
Figure 16:
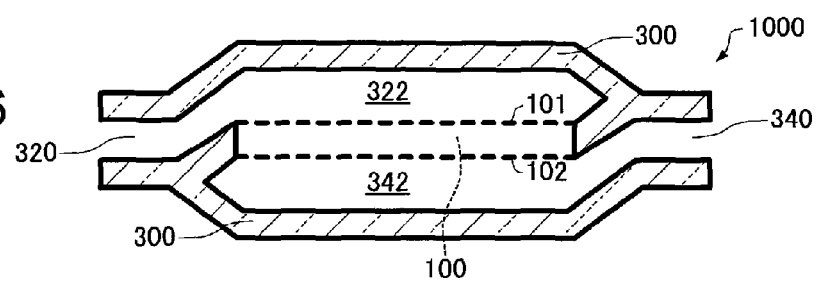
FIG. 16 is a diagrammatic drawing of a cross section of the cell treatment device according to the embodiment.

The cell treatment device 1000 includes the flat-panel shaped slit member 100 and a flow channel forming member 300. FIG. 14 is a plan view diagrammatically showing the cell treatment device 1000 as an example of the cell treatment device in the embodiment. FIG. 15 and FIG. 16 are diagrammatic drawings of cross sections of the cell treatment device 1000. FIG. 15 and FIG. 16 correspond to cross sections taken along the line A-A and the line B-B in FIG. 14, respectively.

The cell treatment device 1000 includes the flow channel forming member 300, and the flow channel forming member 300 is provided with the slit member 100 in the interior thereof. The flow channel forming member 300 forms a flow channel for allowing the cell dispersion liquid to flow therethrough. The flow channel forming member 300 includes a filling port 320 for filling the cell dispersion liquid and a drain port 340 for draining the cell dispersion liquid. The cell treatment device 1000 allows the cell dispersion liquid to pass from the filling port 320 to the drain port 340.

The filling port 320 is in communication with a primary side flow channel 322. The drain port 340 is in communication with a secondary side flow channel 342. The slit member 100 is provided between the primary side flow channel 322 and the secondary side flow channel 342. Therefore, the cell dispersion liquid filled from the filling port 320 passes through the slit member 100 and is guided to the drain port 340.

The slit member 100 is provided so that the first surface 101 faces the primary side flow channel 322 and the second surface 102 faces the secondary side flow channel 342. Therefore, the cell dispersion liquid is capable of passing through the slit member 100 from the first surface 101 side toward the second surface 102 side when passing through the cell treatment device 1000.

The shapes and the sizes of the flow channel forming member 300, the filling port 320, and the drain port 340 are not specifically limited as long as they have the above-described functions. The material of the flow channel forming member 300 is not limited as well. As the material of the flow channel forming member 300, the one similar to the slit member described in "1.3.1. Slit Member" may be selected, and is preferably a material having good biocompatibility. When the flow channel forming member 300 is formed of a material having biocompatibility, for example, damage of normal cells in the cell dispersion liquid may be restrained and, when immune cells are contained in the cell dispersion liquid, the immune cells and the like are prevented from recognizing the flow channel forming member 300 as a foreign substance. In addition, when the cell dispersion liquid is blood, if the biocompatible material is selected as the flow channel forming member 300, the blood coagulating action is restrained. When the flow channel forming member is formed of a material which has low biocompatibility, the surface may be coated with a biocompatible material. As the coating, a coating having at least one of the functions selected from hydrophilic nature, water repellency, and blocking tendency is exemplified.

Figure 17:
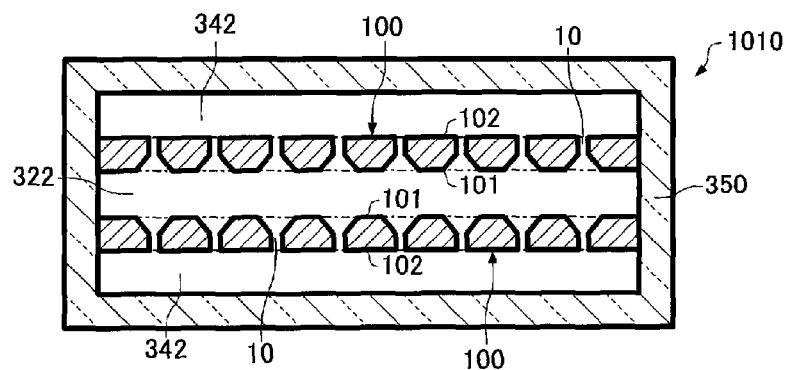
FIG. 17 is a diagrammatic drawing of a cross section of the cell treatment device according to the embodiment.
Figure 18:
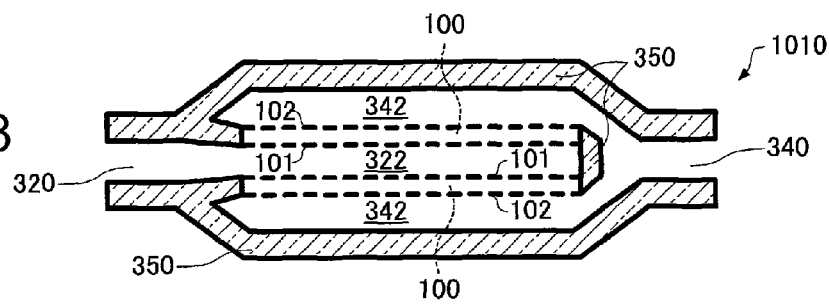
FIG. 18 is a diagrammatic drawing of a cross section of the cell treatment device according to the embodiment.

The cell treatment device including the flat panel-shaped slit member 100 may be modified as follows. FIG. 17 and FIG. 18 are diagrammatic drawings of cross sections of the modification of a cell treatment device 1010. The cell treatment device 1010 includes two slit members 100, and the two slit members 100 are arranged so that the first surfaces 101 oppose to each other. The cell treatment device 1010 includes a flow channel forming member 350. The flow channel forming member 350 forms a flow channel for allowing the cell dispersion liquid to flow therethrough. The flow channel forming member 350 includes the filling port 320 for filling the cell dispersion liquid and the drain port 340 for draining the cell dispersion liquid. The cell treatment device 1010 allows the cell dispersion liquid to pass from the filling port 320 to the drain port 340.

The filling port 320 is in communication with the primary side flow channel 322. The drain port 340 is in communication with the secondary side flow channels 342. The slit members 100 are provided between the primary side flow channel 322 and the secondary side flow channels 342. Therefore, the cell dispersion liquid filled from the filling port 320 passes through the slit members 100 and is guided to the drain port 340.

In the cell treatment device 1010, the two slit members 100 are provided so that the first surfaces 101 face the primary side flow channel 322 and the second surfaces 102 face the secondary side flow channels 342. Therefore, the cell dispersion liquid is capable of passing through any of the slit members 100 from the first surfaces 101 sides toward the second surfaces 102 sides when passing through the cell treatment device 1010.

The shapes and the sizes of the flow channel forming member 350, the filling port 320, and the drain port 340 are not specifically limited as long as they have the above-described functions. The material of a flow channel forming member 370 may be the same as that of the flow channel forming member 300 described above.

The cell treatment device 1010 is configured to supply the cell dispersion liquid to the first surface 101 sides of the two slit members 100 simultaneously. Accordingly, the cell treatment device 1010 is further downsized.

In the examples of the cell treatment device 1000 and the cell treatment device 1010, the slit members 100 are arranged in such a manner that the through holes 10 extend in the direction parallel to the direction from the filling port 320 toward the drain port 340 in plan view. The arrangement of the direction of extension of the through holes 10 is not limited and, for example, arrangement in which the through holes 10 extend in the direction intersecting the direction from the filling port 320 toward the drain port 340 in plan view is also applicable. The arrangement of the slit members 100 may be arranged considering a pressure difference or a pressure loss.

Figure 19:
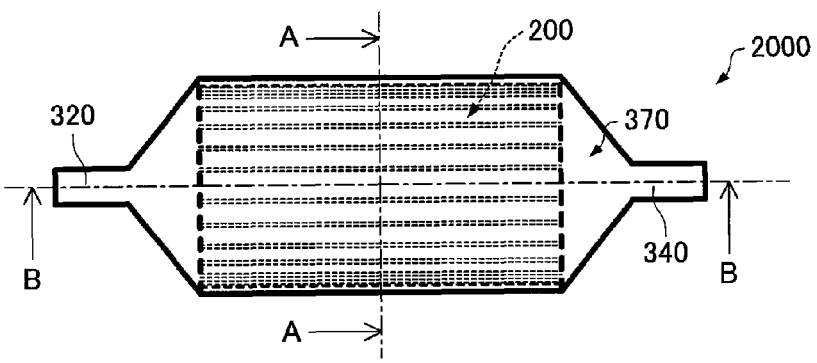
FIG. 19 is a plan view diagrammatically showing a cell treatment device according to an embodiment.
Figure 20:
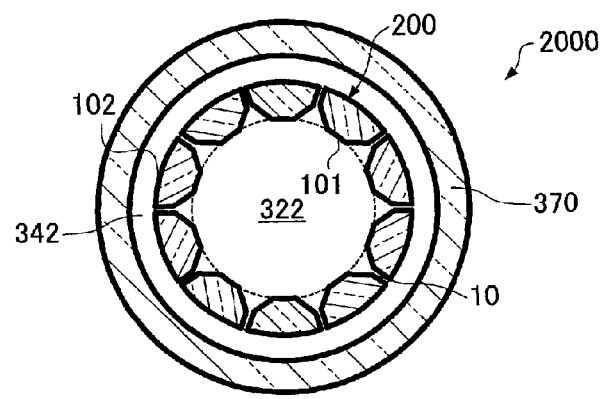
FIG. 20 is a diagrammatic drawing of a cross section of the cell treatment device according to the embodiment.
Figure 21:
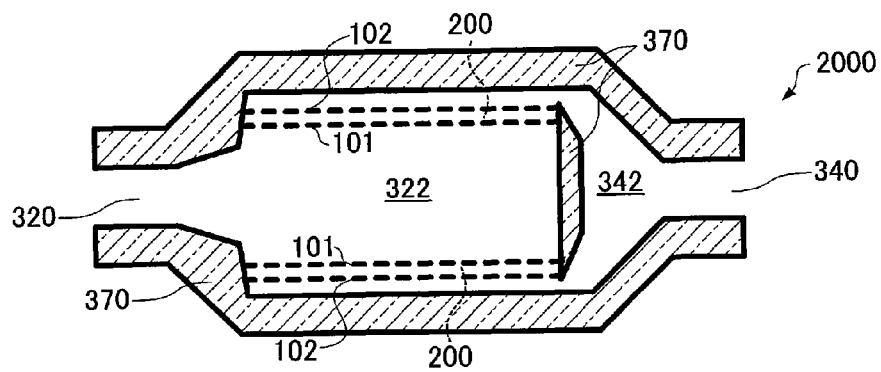
FIG. 21 is a diagrammatic drawing of a cross section of the cell treatment device according to the embodiment.

A cell treatment device 2000 includes the cylindrical slit member 200 and the flow channel forming member 370. FIG. 19 is a plan view diagrammatically showing the cell treatment device 2000 as an example of the cell treatment device in the embodiment. FIG. 20 and FIG. 21 are diagrammatic drawings of cross sections of the cell treatment device 2000. FIG. 20 and FIG. 21 correspond to cross sections taken along the line A-A and the line B-B in FIG. 19, respectively.

The cell treatment device 2000 includes the flow channel forming member 370, and the flow channel forming member 370 is provided with the slit member 200 in the interior thereof. The flow channel forming member 370 forms a flow channel for allowing the cell dispersion liquid to flow therethrough. The flow channel forming member 370 includes the filling port 320 for filling the cell dispersion liquid and the drain port 340 for draining the cell dispersion liquid. The cell treatment device 2000 allows the cell dispersion liquid to pass from the filling port 320 to the drain port 340.

The filling port 320 is in communication with the primary side flow channel 322. The drain port 340 is in communication with the secondary side flow channel 342. The slit member 200 is provided between the primary side flow channel 322 and the secondary side flow channel 342. Therefore, the cell dispersion liquid filled from the filling port 320 passes through the slit member 200 and is guided to the drain port 340.

The slit member 200 is provided so that the first surface 101 faces the primary side flow channel 322 and the second surface 102 faces the secondary side flow channel 342. Therefore, the cell dispersion liquid is capable of passing through the slit member 200 from the first surface 101 side toward the second surface 102 side when passing through the cell treatment device 2000.

The shapes and the sizes of the flow channel forming member 370, the filling port 320, and the drain port 340 are not specifically limited as long as they have the above-described functions. The material of the flow channel forming member 370 may be the same as that of the flow channel forming member 300 described above. FIG. 19 to FIG. 21 show a case in which the inner surface of the cylinder of the slit member 200 is the first surface 101. However, the outer surface of the cylinder of the slit member 200 may be the first surface 101. In such the case, the filling port and the drain port may be exchanged. Accordingly, the cell dispersion liquid is capable of passing through the slit member 200 from the first surface 101 side toward the second surface 102 side when passing through the cell treatment device 2000. Furthermore, although not shown, the cell treatment device 2000 may include the two slit members 200. In this case, in the conceptually same manner as the case of the above-described cell treatment device 1010, passage of the cell dispersion liquid from the first surfaces sides to the second surfaces sides of the two slit members 200 may be achieved by modifying the flow channel forming member.

2. Cell Treatment Cartridge

A cell treatment cartridge according to the embodiment includes the cell treatment device described above, and a plurality of the cell treatment devices are combined to form a single cartridge. The combinations of the cell treatment devices are arbitrary. The plurality of cell treatment devices may have a serial alignment, a parallel alignment, and a combination of the serial and parallel alignments in the cell treatment cartridge.

The cell treatment cartridge as described above is capable of causing at least one of the cancer cells and immune cells to be subjected to at least one of the physical action, the chemical action, and the biologically activating action by allowing cell dispersion liquid including at least one of the cancer cells and the immune cells to pass therethrough.

The cell treatment cartridge having the plurality of cell treatment devices aligned in series is capable of changing the type of the cells to be treated depending on the cell treatment devices. Therefore, a plurality of treatments may be performed by allowing the cell dispersion liquid to pass once therethrough. Also, the cell treatment cartridge including the plurality of cell treatment devices arranged in parallel is capable of increasing the quantity and the flow rate of the cell dispersion liquid to be treated, for example.

The cell treatment cartridge according to the embodiment contributes to facilitating carriage of the cell treatment device. The cell treatment cartridge may be used in a body fluid treatment system described below, for example, and is capable of facilitating a replacement work or the like.

3. Body Fluid Treatment System

Figure 22:
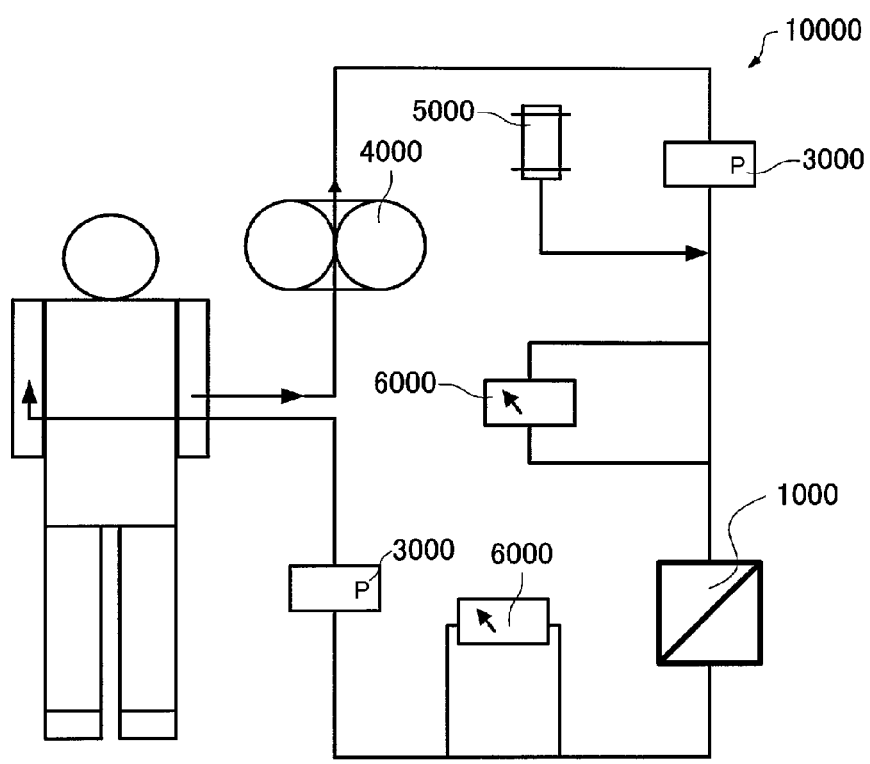
FIG. 22 is a diagrammatic drawing of a cell treatment system according to an embodiment.

A body fluid treatment system 10000 according to the embodiment includes the cell treatment device or the cell treatment cartridge described above. FIG. 22 is a conceptual drawing diagrammatically showing the body fluid treatment system 10000 according to the embodiment. The body fluid treatment system 10000 according to the embodiment is an extracorporeal circulation system configured to take body fluid from the living body, allow cancer cells or immune cells to cause to pass through the above-described cell treatment device or the cell treatment cartridge to cause the same to be subjected to at least one of the physical action, the chemical action, and the biologically activating action and bring the same back to the living body. In the treatment of the cell dispersion liquid by the cell treatment device or the cell treatment cartridge, no specific medical agent or compound is added to the cell dispersion liquid. Therefore, toxicity of the body fluid having passed therethrough may be sufficiently reduced, and safety of the same when feeding back to the living body is ensured.

In the following description, a case where the body fluid treatment system 10000 includes the cell treatment device 1000 will be described. The body fluid treatment system 10000 according to the embodiment preferably includes a pressure monitor 3000 and a pump 4000. The flow rate of the body fluid can be adjusted by the pump 4000 while monitoring the state of the body fluid by the pressure monitor 3000. The pressure monitor 3000 and the pump 4000 may be those which are the same as those used generally in an artificial dialysis. In order to prevent the body fluid from coagulating in a tube, an anticoagulant 5000 may be added.

The body fluid treatment system 10000 according to the embodiment preferably includes monitors 6000 for specifying the number or the type of cancer cells (hereinafter, referred to as "cancer cell monitor") upstream and downstream of the cell treatment device 1000. The cancer cell monitor 6000 installed upstream of the cell treatment device 1000 is configured to record the state of the body fluid before passing through the cell treatment device 1000.

The cancer cell monitor 6000 installed downstream of the cell treatment device 1000 is configured to confirm whether the cancer cells are sufficiently removed, and a state of deterioration of the cancer cell removing capability of the cell treatment device 1000. The cancer cell monitors 6000 are most preferably installed upstream and downstream of the cell treatment device 1000 because whether or not the cancer cells are adequately removed can be evaluated accurately by comparing results of monitoring cancer cells upstream and downstream. However, it is preferable to install the cancer cell monitor 6000 at least upstream of the cell treatment device 1000.

As a device for monitoring cancer cells is not specifically limited, and the known technique may be employed. For example, known techniques as a method of monitoring the number of cancer cells in the flow channel by trapping by the antibody (Specification of U.S. Pat. No. 6,103,479), a method of monitoring cancer cells in the flow channel by trapping by magnetic beads or the like (Japanese Patent No. 3834326), a method of monitoring with electric impedance, a method of determining optically whether it is a cancer cell or not (Specification of U.S. Pat. No. 6,821,484, Specification of U.S. Pat. No. 6,143,535), and a circulating caner call inspective equipment (manufactured by Veridex LLC in U.S.A.) and so on are exemplified. The adequate number of devices, necessity of treatment of the apoptosis factor or the like may be determined from the result of monitoring cancer cells.

For example, when the cell treatment device or the cell treatment cartridge described above is applied, the ratio of existence of cancer cells in the body fluid may be reduced to a density which has no possibility of transfer or lower. Since the used cell treatment device 1000 including dangerous cancer cells can be cut off from the route of the extracorporeal circulation system, it can be discarded as it is. By discarding the used cell treatment device 1000, the removed cancer cells are prevented from being returned into the living body by entering the rout of the extracorporeal circulation system. Also, by inspecting the cancer cells trapped in the used cell treatment device 1000, it may be helpful for medical treatment or precaution.

In the description of the body fluid treatment system 10000 described above, the treatment of the body fluid taken from the living body is exemplified. However, the body fluid treatment system 10000 is not limited to such the treatment and, for example, it may be applied to a case of manufacturing blood preparation from blood.

It is easily understood that an object of application of the cell treatment device, the cell treatment cartridge, and the body fluid treatment system according to the invention is not limited to the cancer cells and the immune cells, and the invention is applied generally to microorganisms such as bacteria or the like. The cell treatment device in the embodiment may also be applied for separating or detoxifying virus, protein, low polymer to high polymer molecules, colloid particles, allergic substances (pollen and the like), and toxic substances.

The invention is not limited to the embodiment described above, and various modifications may be made. For example, the invention includes the substantially same configuration as the configuration described in the embodiment (for example, the configuration in which the function, the method and the result are the same, or the configuration having the same object or the effect). The invention includes also the configuration in which portions which are not essential in the configuration described in the embodiment are replaced. The invention also includes configurations which achieves the same effects and advantages as the configurations described in the embodiment, and configurations which are capable of achieving the same object. The invention also includes a configuration in which publicly known techniques are added to the configuration described in the embodiment.

What is claimed is:

1. A cell treatment device which allows cell dispersion liquid including cancer cells to pass therethrough to cause at least the cancer cells to be subjected to at least one of a physical action, a chemical action, and a biologically activating action, comprising:
a slit member having a first surface and a second surface opposite to each other, the slit member having a slit-through hole that is in an elongated slit shape penetrating from the first surface to the second surface in a first direction, the slit-through hole having a tapered portion, wherein
a first width of a first cross section of the tapered portion orthogonal to the first direction reduces from the first surface toward the second surface, and a width of a cross section adjacent to the second surface is smaller than an average diameter of the cancer cells,
a length of the slit-through hole is longer than the first width,
the cell dispersion liquid is allowed to pass from the first surface to the second surface through the slit-through hole,
the slit member is in a cylindrical shape and has first and second outer periphery sides which are opposed to each other, and
the slit-through hole is longitudinally and continuously extended in a length direction of the slit member orthogonal to the first direction so that the length of the slit-through hole in the length direction is substantially the same as a length between the first and second outer periphery sides of the slit member.

2. The cell treatment device according to claim 1, wherein the first surface and the second surface are parallel to each other.

3. The cell treatment device according to claim 1, wherein the slit-through hole further includes a narrowed portion,
the narrowed portion is located between the second surface and the tapered portion, and
a second width of a second cross section of the narrowed portion orthogonal to the first direction is smaller than the first width.

4. The cell treatment device according to claim 3, the narrowed portion includes a first area on the first surface side and a second area on the second surface side, and
the width of a cross section of the second area orthogonal in the one direction is smaller than an average diameter of the immune cells included in the cell dispersion liquid.

5. The cell treatment device according to claim 4, wherein an immune cell activating factor which acts specifically on the immune cells is fixed to the surface of the slit member which forms the second area.

6. The cell treatment device according to claim 3, wherein a cytokine which acts on the cancer cells is fixed to the surface of the slit member which forms the narrowed portion.

7. The cell treatment device according to claim 6, wherein the cytokine is an apoptosis factor.

8. The cell treatment device according to claim 1, wherein the through hole further has an inverted tapered portion,
the inverted tapered portion continues to an end of the tapered portion or the narrowed portion on the second surface side, and
the width of a cross section of the inverted tapered portion orthogonal in the one direction increases from the first surface side toward the second surface.

9. The cell treatment device according to claim 1, wherein an antibody which acts specifically on the cancer cells is fixed to the surface of the slit member which forms the tapered portion.

10. The cell treatment device according to claim 1, wherein the surface of the slit member which forms the tapered portion includes a groove.

11. The cell treatment device according to claim 1, wherein a coating having at least one of functions selected from hydrophilic nature, water repellency, and blocking tendency is applied on the surface of the slit member.

12. The cell treatment device according to claim 1, wherein the slit member is formed with a plurality of the through holes extending in parallel with each other.

13. The cell treatment device according to claim 1, comprising:
two of the slit members,
wherein the two slit members are arranged so that the first surfaces face each other.

14. A cell treatment cartridge which allows cell dispersion liquid including cancer cells to pass therethrough to cause at least the cancer cells to be subjected to at least one of a physical action, a chemical action, and a biologically activating action, comprising:
a slit member having a first surface and a second surface opposite to each other, the slit member having a slit-through hole that is in an elongated slit shape penetrating from the first surface to the second surface in a first direction, the slit-through hole having a tapered portion, wherein
a width of a cross section of the tapered portion orthogonal to the first direction reduces from the first surface toward the second surface, and a width of a cross section adjacent to the second surface is smaller than an average diameter of the cancer cells,
a length of the slit-through hole is longer than the width,
the cell dispersion liquid is allowed to pass from the first surface to the second surface through the slit-through hole,
the slit member is in a cylindrical shape and has first and second outer periphery sides which are opposite to each other, and
the slit-through hole is longitudinally and continuously extended in a length direction of the slit member orthogonal to the first direction so that the length of the slit-through hole in the length direction is the same as a substantial length between the first and second outer periphery sides of the slit member.

15. A cell treatment cartridge which allows cell dispersion liquid including cancer cells to pass therethrough to cause at least the cancer cells to be subjected to at least one of a physical action, a chemical action, and a biologically activating action, comprising:
a slit member having a first surface and a second surface opposite to each other, the slit member having a slit-through hole that is in an elongated slit shape penetrating from the first surface to the second surface in a first direction, the slit-through hole having a tapered portion, wherein
the slit member is in a cylindrical shape and has first and second outer periphery sides which are opposite to each other, and
the slit-through hole is longitudinally and continuously extended in a length direction of the slit member orthogonal to the first direction so that a length of the slit-through hole in the length direction is the same as a substantial length between the first and second outer periphery sides of the slit member.

16. A cell treatment cartridge which allows cell dispersion liquid including cancer cells, white blood cells, red blood cells, and platelets to pass therethrough to cause the cancer cells to be subjected to at least one of a physical action, a chemical action, and a biologically activating action, comprising:
   a slit member having a first surface and a second surface opposite to each other, the slit member having a slit-through hole that is in an elongated slit shape penetrating from the first surface to the second surface in a first direction, the slit-through hole having a tapered portion, wherein
   a width of a cross section of the tapered portion orthogonal to the first direction reduces from the first surface toward the second surface, wherein a first width of a cross section adjacent to the first surface is larger than an average diameter of the cancer cells and a second width of a cross section adjacent to the second surface is smaller than an average diameter of the cancer cells, but larger than average diameters of white blood cells, red blood cells and platelets,
   a length of the slit-through hole is longer than the width,
   the cell dispersion liquid including the white blood cells, red blood cells, and platelets is allowed to pass from the first surface to the second surface through the slit-through hole,
   the slit member is in a cylindrical shape and has first and second outer periphery sides which are opposite to each other, and
   the slit-through hole is longitudinally and continuously extended in a length direction of the slit member orthogonal to the first direction so that the length of the slit-through hole in the length direction is the same as a substantial length between the first and second outer periphery sides of the slit member.

17. The cell treatment cartridge according to claim 16, wherein the second width of the cross section adjacent to the second surface is from 22 μm to 32 μm.

* * * * *